United States Patent

Obel

[11] Patent Number: 5,836,984
[45] Date of Patent: Nov. 17, 1998

[54] HEART STIMULATING DEVICE

[75] Inventor: Martin Obel, Danderyd, Sweden

[73] Assignee: Pacesetter AB, Järfälla, Sweden

[21] Appl. No.: 954,688

[22] Filed: Oct. 20, 1997

[30] Foreign Application Priority Data

Oct. 21, 1996 [SE] Sweden ................... 9603865

[51] Int. Cl.⁶ .................................. A61N 1/00
[52] U.S. Cl. .................................. 607/9
[58] Field of Search ................. 607/9, 14, 27, 607/17, 11

[56] References Cited

U.S. PATENT DOCUMENTS 4,969,467  11/1990  Callaghan et al. .
5,351,696  10/1994  Riff et al. .

Primary Examiner—Scott M. Getzow
Attorney, Agent, or Firm—Hill & Simpson

[57] ABSTRACT

A heart stimulating device for avoiding problems related to fusion beats contains a pulse generator for delivering stimulation pulses to a patient's heart and having a basic escape interval, a detector with a filter which senses QRS characteristics in IEGM signals, a logic stage which controls the pulse generator, and a detector without a filter which senses QRS characteristics in IEGM signals. The logic stage activates the detector without a filter preceding an end of the basic escape interval and prolongs the basic escape interval by a predetermined extension interval if the detector without a filter senses a QRS indication.

7 Claims, 2 Drawing Sheets

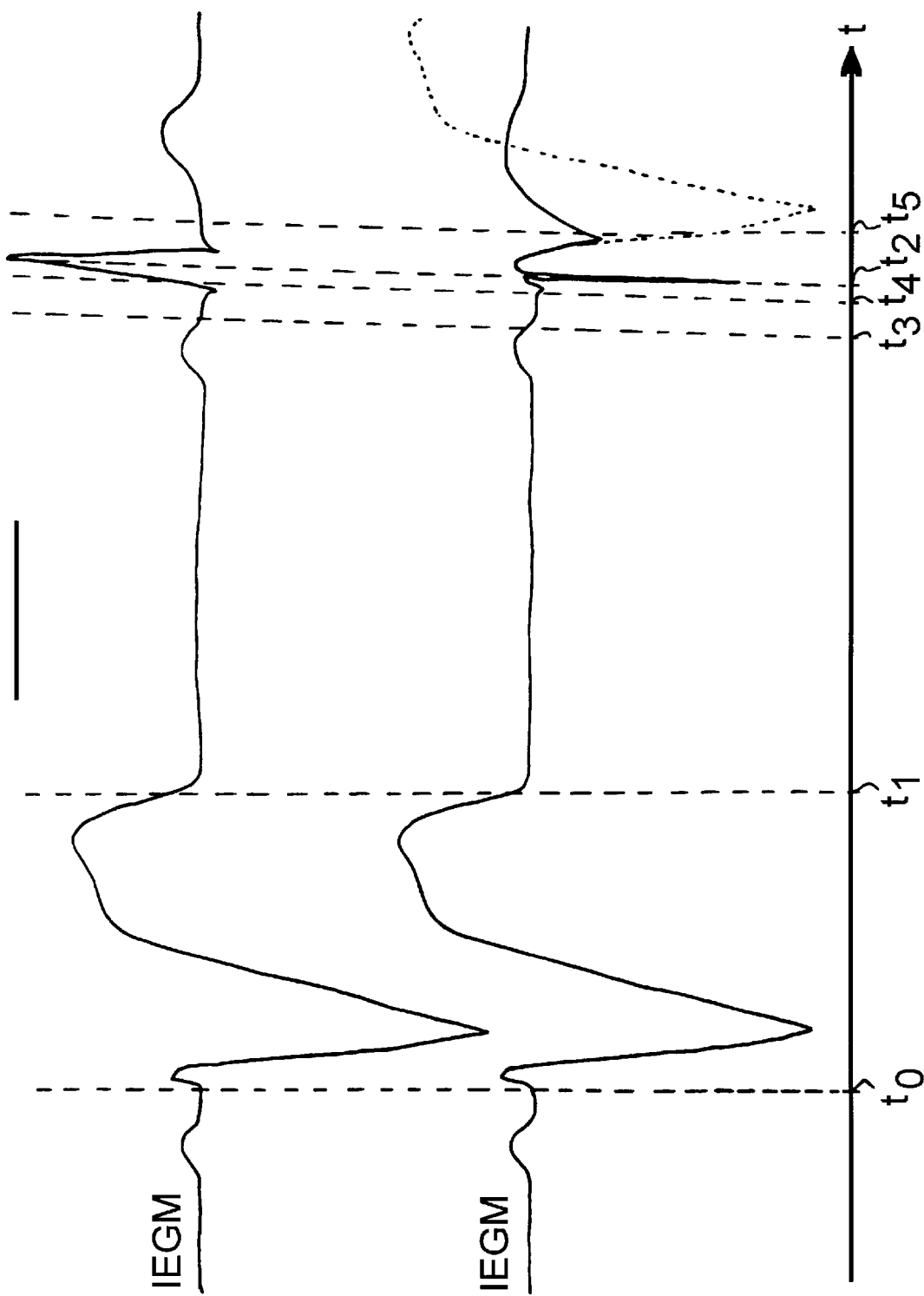

HEART STIMULATING DEVICE

BACKGROUND OF THE INVENTION

1. Field of the Invention

The present invention relates to a heart stimulating device OF THE TYPE having a capability to inhibit stimulation in case of natural activity of a patient's heart. The invention particularly concerns the capability of detecting intrinsic events in order to favor intrinsic heart activity and to avoid fusion beats.

2. Description of the Prior Art

"Fusion beat" generally refers to a situation where atrial or ventricular depolarization starts from two different locations in the heart. Such a situation arises when a natural heart beat occurs simultaneously with an electrical stimulation pulse from a heart stimulating device and they both contribute to the depolarization of a heart chamber.

In demand pacemakers or other heart stimulating devices that aim to electrically stimulate a patient's heart only in the absence of a normal intrinsic function, fusion beats or pseudofusion beats present a particular problem, since intrinsic events are to be favored and stimulation energy is to be saved until really needed. The longevity of a battery powered heart stimulating device is thereby improved.

Some terminology used herein is explained below.
IEGM: An abbreviation for intracardiac electrogram. IEGM signals are emitted by active cardiac tissue and sensed through electrodes placed on or within the heart.
QRS or QRS complex: The ventricular depolarization as seen on the electrocardiogram or in the IEGM signals.
Intrinsic: Inherent or belonging to the heart itself. An intrinsic beat is a naturally occurring heartbeat.
R-wave: An intrinsic ventricular event. R-wave refers to the entire intrinsic QRS complex.
Evoked response: The electrical activation of the myocardium by a pacemaker output pulse. The ability of cardiac tissue to respond depends on its activity state.
Fusion beat: the pacemaker impulse appears close to a spontaneous QRS complex and partly affects the ventricular depolarization.
Pseudofusion beat: the pacemaker impulse appears within a spontaneous QRS complex and does not affect the ventricular depolarization. May be referred to as simply a fusion beat in contexts where problems related thereto are similar to those of regular fusion beats.
Hysteresis: A programmable feature in some demand pacemakers which allows programming of a hysteresis escape rate lower than the programmed base rate. Hysteresis may be accomplished by prolonging the pacing interval following a sensed intrinsic beat.
Escape interval, basic interval, or basic escape interval): The period, typically in the order of 1000 milliseconds, between a sensed intrinsic cardiac event or a stimulation pulse output and the next pacemaker output pulse.

In today's pacemakers of the inhibition type, e.g., in Pacesetter® REGENCY™ pacemakers with AUTOCAPTURE™, IEGM signals are sensed via a lead and electrode arrangement. Intrinsic and stimulated QRS indications in the IEGM signals are monitored by sensing circuitry in the pacemaker. As long as intrinsic QRS complexes are detected at an acceptable rate by the sensing circuitry, the pacemaker inhibits the stimulation pulses. At each detected intrinsic QRS, a timer is started in the pacemaker. If no new QRS is detected within a predetermined basic interval of the timer, a stimulation pulse to the heart is emitted by a pulse generator in the pacemaker. The QRS detections are performed after a bandpass filter that delays the IEGM signals. If an intrinsic QRS occurs immediately before the end of a basic escape interval, it will not be noticed before the next stimulation pulse is transmitted. when that stimulation pulse is transmitted, the pacemaker will have difficulties in detecting the QRS and, as a result of the non-detection, the pacemaker may react by increasing its output energy, even though such an increase is not needed. These problems become more severe if the intrinsic heart rhythm is somewhat faster than that of the pacemaker. A continuous state of this type could be avoided by using so-called hysteresis.

The above described situation, however, is problematic in known stimulation devices and may lead to a higher energy consumption rate than necessary since the heart stimulating device emits pulses that are not required. Also, the energy of the stimulation pulses may erroneously be set higher than necessary. An excessively high energy consumption will cause premature depletion of the battery of the stimulation device resulting in higher risk and inconvenience to the patient. A stimulation device which is capable of safely distinguishing between a true capture failure and a fusion beat is thus highly desirable.

SUMMARY OF THE INVENTION

It is an object of the present invention to provide a solution to the above-mentioned shortcomings of the prior art. A particular object is to provide a stimulation device which avoids fusion beats more effectively. Another object of the invention is to provide a stimulation device which avoids excessive energy in the stimulation pulses.

The above objects are achieved in accordance with the principles of the present invention in a heart stimulating device having a pulse generator which delivers stimulation pulses to a patient's heart with a basic escape interval associated with the pulses, a detector containing a filter which senses QRS indications in incoming IEGM signals, a detector without a filter which also senses QRS indications in the IEGM signals. The heart stimulating device has a logic stage which activates the detector without a filter preceding the end of the basic escape interval, and prolongs the basic escape interval by a predetermined extension interval if the detector without a filter senses a QRS indication.

DESCRIPTION OF THE DRAWINGS

FIG. 2 shows two examples of IEGM signals for explaining the operation of the device of FIG. 1, illustrating situations where a fusion beat occurs due to filter delay in sensing an R-wave and where stimulation is inhibited according to the invention as a result of a detected competing intrinsic event, respectively.

DESCRIPTION OF THE PREFERRED EMBODIMENTS

Figure 1:
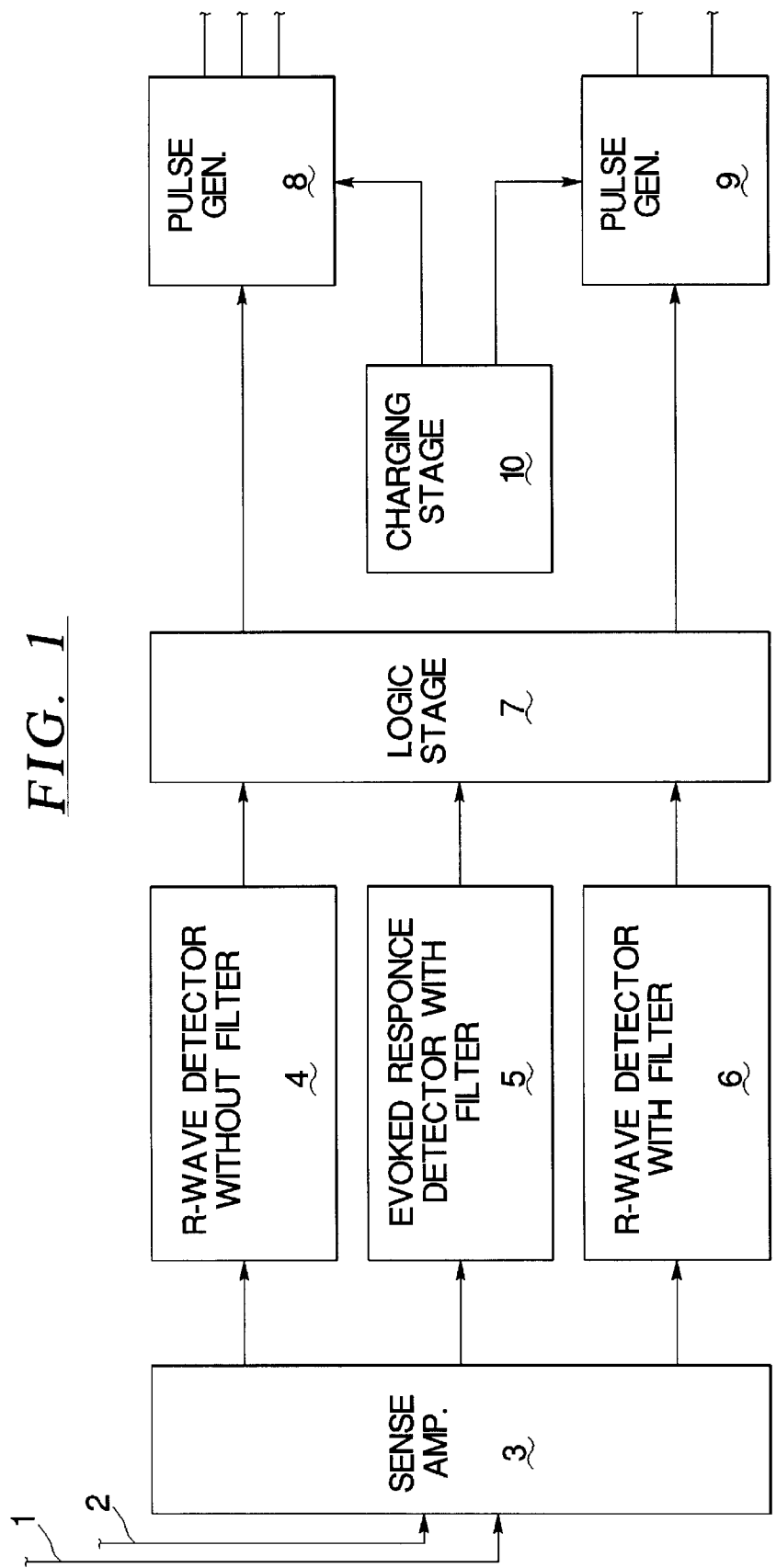
FIG. 1 shows a block diagram of a heart stimulating device according to one embodiment of the invention.

To describe an embodiment of a heart stimulating device according the invention, reference is are made to FIG. 1. The described type of device is operable to inhibit stimulation to favor intrinsic events. The device has sensing inputs 1 and 2 that feed IEGM signals to a sense amplifier 3. The sensing inputs 1 and 2 are typically connected to a lead (not shown) and a cardiac electrode (not shown) which provide the IEGM signals to the heart stimulating device. The sense amplifier provides amplified IEGM signals to three detectors 4, 5 and 6. A first R-wave detector 4 with a filter is operable to detect intrinsic QRS complexes. It could also have the ability to detect P waves if processing thereof is to be performed by the heart stimulating device. An evoked response (ER) detector 5, also with a filter, is operable to detect stimulation-evoked QRS complexes. A non-filtered second R-wave detector 6 is operable to detect intrinsic QRS complexes. Each of the detectors 4, 5 and 6 is connected to a logic stage 7, the detectors 4, 5 and 6 respectively indicate a detected QRS complex to the logic stage 7.

In order to obtain a reliable detection of QRS complexes, possible noise such as myopotentials and external electromagnetic disturbance has to be prevented from influencing the detection. For this purpose, the first R-wave detector 4 includes a bandpass filter for filtering the amplified IEGM signals before they are used for detection of QRS complexes. In the bandpass filter there is, however, inevitably a delay or transit time for the signals. In today's pacemakers such a delay may be 20 ms. Although the filter delay time may be the most significant one, all unintended signal delays in the heart stimulating device could be a problem when aiming to avoid fusion beats or the negative consequences thereof. An example of such a delay is the transit time of the stimulation inhibition signal.

The logic stage 7 controls a pacing pulse generator 8 and a back-up pulse generator 9 which are operable to transmit stimulation pulses to a patient's heart. The pulse generators 8 and 9 may be connected to the same lead (not shown) to the same cardiac electrode (not shown) as the sense amplifier 3. A charging stage 10 is connected to both pulse generators 8 and 9 to provide them with the necessary stimulation energy.

The logic stage 7 includes a timer in order to stimulate the patient's heart at an appropriate rate when needed and to distinguish between the different detections made in the detectors 4, 5 and 6. The logic stage 7 may also deactivate any of the detectors 4, 5 and 6 during selected time intervals.

The delay in the first R-wave detector 4 implies that a decision by the logic stage 7 to initiate a stimulation pulse can only be based on signals representing a situation up until the present time minus the filter delay. In order for the heart stimulating device to maintain a selected pacing rate, the logic stage 7 has to decide, after a certain time interval has passed since a detected QRS complex, whether a stimulation pulse should be transmitted. This time interval will be referred to as a basic interval. Thus, when stimulation control is based on filtered signals, an intrinsic heart beat occurring within a filter delay time from the end of a basic interval will not lead to inhibition of a stimulation pulse.

The non-filtered R-wave detector 6 gives an earlier detection of a QRS complex, but suffers from a higher sensitivity to noise. As will be further described below a combination of the two R-wave detectors 4 and 6 is particularly advantageous.

References will now also be made to FIG. 2 which includes an upper IEGM curve including one stimulation-evoked and one intrinsic QRS complex, and a lower IEGM curve including first a stimulation-evoked QRS complex and then a fusion beat, i.e., an intrinsic event wherein a stimulation pulse has been transmitted. The dotted line indicates an expected curve shape in the absence of an intrinsic heart activity. FIG. 2 further shows a time line on which points in time $t_0$, $t_1$, $t_2$, $t_3$, $t_4$ and $t_5$ have been marked with dashed lines to indicate, respectively, a transmission of a stimulation pulse to evoke a QRS ($t_0$), an end point for detecting evoked response subsequent to a stimulation ($t_1$), an end of a basic interval simultaneously with an intrinsic QRS complex ($t_2$), the activation of the non-filtered detector 6 ($t_3$), the instant when the non-filtered detector 6 detects the intrinsic event ($t_4$), and an end of a prolonged basic interval ($t_5$).

In order to illustrate the operation of the inventive heart stimulating device, a sequence to be described is assumed to start by the transmission of a stimulation pulse at $t_0$. The evoked response detector 5 then is activated after a predetermined delay to detect evoked response until $t_1$. If no evoked response has been detected, the heart stimulating device generally emits a back-up pulse.

At $t_2$, which is the end of the basic interval ranging from $t_0$ to $t_2$, the upper IEGM curve indicates an intrinsic event and an inhibition of stimulation, while the lower curve indicates a fusion beat.

According to the invention, the detector is active for only about 20 ms from $t_3$ until the end of the basic interval at $t_2$ or only until a detection of an intrinsic event at $t_4$. If an intrinsic event is detected in the non-filtered detector between $t_3$ and $t_2$, the basic interval is prolonged until $t_5$, so that the IEGM signal containing the intrinsic QRS indication will have time to travel through the filter of the R-wave detector 4. For this reason, an extension interval from $t_2$ to $t_5$ can be set equal or greater than the filter delay time. Alternatively, the point in time $t_5$ when the prolonged escape interval ends can be set by $t_4$, i.e., the point in time at which the detector 6 detects an intrinsic QRS.

A subsequent basic interval is started at $t_2$ and the length thereof may be set equal to the preceding one in order to maintain a pacing rate, or may be set so that hysteresis is achieved which favors intrinsic events.

The safe operation of the inventive heart stimulating device is effectively maintained since a basic interval would be prolonged mainly in exceptional situations and the prolongation would be very small compared to the length of a typical heart cycle.

A typical length of the basic interval is 850 ms, it could have an adjustment range between 500 and 1333 ms. The bandpass filter delay, which is to be compensated for, in the filtered R-wave detector 4 is typically 20 ms. Consequently, following a detection in the R-wave detector 6 of an intrinsic QRS, the basic interval should typically be 20 ms or slightly more immediately after the end of the basic interval or, if a varying timing is not unsuitable, after the detection in the R-wave detector 6.

The activation time of the R-wave detector 6 has to precede the "blind" interval of the detector 4 before the end of the basic interval. Therefore, it will typically be at least 20 ms or slightly more before the end of the basic interval. Since, however, the R-wave detector only controls the prolongation of the basic interval and not the stimulation inhibition itself, it could be longer. For energy saving reasons, it is kept short.

It should be noted that FIG. 2 is not drawn to scale but rather illustrates the relative timing of typical phenomena monitored through the IEGM signals.

Although modifications and changes may be suggested by those skilled in the art, it is the intention of the inventor to embody within the patent warranted hereon all changes and modifications as reasonably and properly come within the scope of his contribution to the art.

I claim as my invention:

1. A heart stimulating device comprising:
   a pulse generator which emits stimulation pulses, each stimulation pulse being preceded by a basic escape interval;

lead means adapted for interaction with cardiac tissue for delivering said stimulation pulses to cardiac tissue and for obtaining IEGM signals from cardiac tissue;

first sensing means containing a filter, and connected to said lead means, for sensing QRS indications in said IEGM signals;

second sensing means without a filter, and connected to said lead means, for sensing QRS indications in said IEGM signals; and control means connected to said first sensing means, said second sensing means and said pulse generator, for activating said second sensing means preceding an end of each basic escape interval and for prolonging said basic escape interval in said pulse generator by a predetermined extension interval if said second sensing means senses a QRS indication when activated.

2. A heart stimulating device as claimed in claim 1 wherein said first sensing means has a filter delay associated therewith, and wherein said control means comprises means for prolonging said basic escape interval in said pulse generator by a fixed amount which is substantially equal to or greater than said filter delay.

3. A heart stimulating device as claimed in claim 1 wherein said control means comprises means for setting a length of said extension interval dependent on a time at which said second sensing means senses said QRS indication.

4. A heart stimulating device as claimed in claim 3 wherein said first sensing means has a filter delay associated therewith, and wherein said control means comprises means for setting said extension interval substantially equal to said filter delay minus a remainder of the basic escape interval at said time at which said second sensing means senses said QRS indication.

5. A heart stimulating device as claimed in claim 1 wherein said control means comprises means for setting a length of said basic escape interval dependent on whether said QRS indication is associated with an intrinsic heartbeat or a stimulation pulse-evoked heartbeat.

6. A heart stimulating device as claimed in claim 1 wherein said control means comprises means for activating said second sensing means after at least 95% of said basic escape interval has elapsed.

7. A heart stimulating device as claimed in claim 1 wherein said control means comprises means for activating said second sensing means 20 ms or less before said end of said basic escape interval.

* * * * *